(12) United States Patent
Zhuo

(10) Patent No.: US 11,541,060 B2
(45) Date of Patent: Jan. 3, 2023

(54) PHARMACEUTICAL COMPOSITIONS FOR TREATING PAIN

(71) Applicant: FOREVER CHEER INTERNATIONAL LIMITED, Hong Kong (HK)

(72) Inventor: Min Zhuo, Hong Kong (HK)

(73) Assignee: FOREVER CHEER HOLDING LIMITED, Sheung Wan (HK)

( * ) Notice: Subject to any disclaimer, the term of this patent is extended or adjusted under 35 U.S.C. 154(b) by 0 days.

(21) Appl. No.: 16/871,628

(22) Filed: May 11, 2020

(65) Prior Publication Data

US 2020/0268766 A1 Aug. 27, 2020

Related U.S. Application Data

(63) Continuation of application No. 15/984,410, filed on May 20, 2018, now abandoned.

(30) Foreign Application Priority Data

May 20, 2017 (JP) .................................. 2017-100431

(51) Int. Cl.
| | |
|---|---|
| *A61K 31/5377* | (2006.01) |
| *A61K 31/485* | (2006.01) |
| *A61K 31/52* | (2006.01) |
| *A61P 25/22* | (2006.01) |
| *A61K 45/06* | (2006.01) |
| *A61P 25/24* | (2006.01) |
| *A61P 25/04* | (2006.01) |
| *A61P 25/00* | (2006.01) |
| *A61P 25/30* | (2006.01) |
| *A61P 29/02* | (2006.01) |

(52) U.S. Cl.
CPC ........ *A61K 31/5377* (2013.01); *A61K 31/485* (2013.01); *A61K 31/52* (2013.01); *A61K 45/06* (2013.01); *A61P 25/00* (2018.01); *A61P 25/04* (2018.01); *A61P 25/22* (2018.01); *A61P 25/24* (2018.01); *A61P 25/30* (2018.01); *A61P 29/02* (2018.01)

(58) Field of Classification Search
CPC .. A61K 31/52; A61K 31/5377; A61K 31/485; C07D 487/04
See application file for complete search history.

(56) References Cited

U.S. PATENT DOCUMENTS

| | | | |
|---|---|---|---|
| 8,124,599 | B2 | 2/2012 | Zhou |
| 9,963,457 | B2 * | 5/2018 | Zhuo ...................... A61P 25/02 |
| 2009/0233922 | A1 | 9/2009 | Zhou |
| 2011/0098295 | A1 | 4/2011 | Zhou |

OTHER PUBLICATIONS

Zhuo (Drug Discovery Today, Jun. 2012, vol. 17, Nos. 11/12, pp. 573-582) (Year: 2012).*
Song et al. BMC Anesthesiology, 2015, 15:12, 8 pages (Year: 2015).*
Ahmadi et al. Iran J. Basic Med. Sci., 2016; 19:924-931 (Year: 2016).*
Li et al. Mol. Pharmacol., 2006, vol. 70, pp. 1742-1749 (Year: 2006).*

* cited by examiner

*Primary Examiner* — James D. Anderson
(74) *Attorney, Agent, or Firm* — Dragon Sun Law Firm, PC; Jinggao Li; Nathaniel Perkins

(57) ABSTRACT

The present invention discloses a novel use of a pharmaceutical composition in the preparation of a medicament in the treatment of opioid-induced tolerance and addiction, in particular to the use of AC1 inhibitor NB001 and AC1&8 mixed inhibitors NB010 and NB011 in the preparation of a medicament in the treatment of opioid-induced tolerance and addiction.

8 Claims, 4 Drawing Sheets

Morphine tolerance test

Place preference

PHARMACEUTICAL COMPOSITIONS FOR TREATING PAIN

CROSS-REFERENCE TO RELATED APPLICATIONS

This application is a continuation of and claims priority to U.S. patent application Ser. No. 15/984,410 with a filing date of May 20, 2018, which claims priority to Japanese Patent Application 2017100431 with a filing date of May 20, 2017. The contents of the aforementioned applications, including any intervening amendments thereto, are incorporated herein by reference.

FIELD OF THE INVENTION

The present invention relates to a novel use of a pharmaceutical composition for preparing a medicament in the treatment of opioid-induced tolerance and addiction, in particular to use of AC1 inhibitor NB001 and AC1&8 mixed inhibitors NB010 and NB011 for preparing a medicament in the treatment of opioid-induced tolerance and addiction.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, morphine is often used to relieve some of the severe pain, however, the clinical use of morphine is limited by the development of analgesic tolerance, physical dependency, and addiction. It is known that long-term administration of morphine may induce tolerance in humans and animals but does not desensitize μ-receptors. In contrast, long-term use of morphine may lead to hypersensitization of adenylyl cyclase (AC), which contributes to opioid tolerance and dependency (Nestler, 1997; 2001a, b; 2002). Long-term changes in adenylyl cyclase activity in several brain regions have been reported, such as the ventral tegmental area (VTA) and the nucleus accumbens (NAc) area (both of which are critical for consolidating opium medicament) within the mid-brain, as well as in the locus coeruleus and dorsal nucleus (critical for opium withdrawal) (Nestler and Aghajanian, 1997; Jolas et al., 2000; Williams et al., 2001; Chao and Nestler, 2004).

Although the role of ACs in modulating opioids has been suggested, the lack of specific inhibitors to define the role of different AC isoenzymes has led to a relative slow progress in research. To date, genes of 10 ACs have been cloned, each with a different expression pattern in the central nervous system and peripheral sensory nervous system (Xia and Storm, 1997). Among them, AC1 and AC8 are exclusively stimulated by Ca 2+/calmodulin in the brain. AC1 and AC8 are widely distributed in different brain regions, including VTA, NAc, locus coeruleus, and dorsal raphe nucleus (Zhuo, 2012).

In addition, many studies have involved CREB in drug addiction (Guitart et al., 1992; Hyman, 1996; Maldonado et al., 1996; Walters et al., 2001). Western blot analysis showed increased expression of CREB or phosphorylated CREB (pCREB) in morphine-tolerant animals (Li et al., 1999; Gao et al., 2004). CREB-mutated mice showed less severe withdrawal symptoms after morphine treatment was discontinued (Maldonado et al., 1996). In addition, the G protein-coupled receptor M opioid receptor (MOR), which essentially mediates the physiologic effects of morphine, comprises CRE elements and has been proved to be activated via the CREB-mediated pathway (Min et al., 1994; Nestler, 1997. Lee et al., 2003). In the central nervous system, AC1 and AC8 are known to act on upstream key signaling proteins to regulate CREB in neurons (Wei et al., 2002; Zhuo, 2012). Through the use of AC1 and AC8 knockout (KO) mice, and DKO mice, it is reported that there is no difference in the analgesic effect of morphine in short-term in the AC1 or AC8 knockout mice, or DKO mice and wild-type mice (Li et al., 2006). AC1 &8 DKO mice and AC8 knockout mice continued to induce reduced tolerance by daily injections of morphine (10 mg/kg body weight). In DKO mice treated with morphine continuously, the withdrawal behavior was significantly reduced (Li et al., 2006). A recent study using a AC1 inhibitor ST034037 found that AC1 activity does require AC sensitization induced by chronic activation of MOR, suggesting that AC1 inhibition may be beneficial to overcome chronic morphine induced tolerance and other responses (Brust et al., 2017).

During the treatment of pain by using opioids, the decline in efficacy is often explained by pharmacological tolerance mechanisms (or exacerbation of the original condition), and the dose must be increased to maintain the original efficacy. Recent studies have confirmed that opioids, in addition to producing analgesic effects, can also activate the in vivo mechanisms of promoting harm, leading to increased body sensitivity to pain, namely opioid-induced hyperalgesia (OIH). Onset of sensitivity to pain was observed early in the opioid withdrawal response. The latest evidence suggests that sensitivity to pain may also occur during opioid treatment. In other words, the discontinuation of opioids and the continued administration of opioids both result in an increase in pain sensitivity, which is clearly contradictory. Therefore, the decrease of opioid analgesic effect is likely to be the role of OIH (the mechanism of promoting harm), and not just the mechanism of pharmacological tolerance. Among them, both sensitization processes and desensitization processes occur. OIH has its unique cellular mechanism involving endogenous dynorphin, glutamatergic systems, and descending facilitation mechanisms. Interestingly, the mechanism of OH is largely overlapped with the mechanism of neuropathic pain and opioid tolerance. For example, peripheral nerve injury and repetitive opioid administration can activate the same glutamatergic cellular pathway.

The decline in the effectiveness of drug analgesia during opioid therapy is considered to be a pharmacological tolerance or an increase in existing pain status. Therefore, the addition of drug doses is taken for granted the only choice for the reconstitution of drug effects. However, according to a contradictory evidence provided by the clinical and laboratory research institute for opioid-induced pain, the inventor must reconsider the explanation to this phenomenon. On the one hand, if the decrease in opioid efficacy is related to the drug tolerance mechanism, then it is obviously beyond reproach to increase the dose; on the other hand, if the decrease is due to OIH, to increase the dose blindly will only enhance the in vivo process for promoting harm, thereby increase pain and tolerance.

Accordingly, it is significantly important for the research and development of new medicament or combination preparations in order to prolong the pain relief of opioids and overcome the analgesic tolerance, physical dependency, and addiction in clinical applications.

PRIOR ART LITERATURE

Non-Patent Literature

Brust et al (2017) Identification of a selective small-molecule inhibitor of type 1 adenylyl cyclase activity with analgesic properties. Science signaling 10.

Patent Literature

U.S. Patent Publication No. US2011/0098295

SUMMARY OF THE INVENTION

Technical Problems to be Solved by the Invention

In view of the problems of analgesic tolerance, physical dependency, and addiction of the above-mentioned opioids, the present invention is directed to develop a novel medicament or combination preparation for reducing or improving the problem of analgesic tolerance, physical dependency, and addiction caused by long-term use of opioids, that is to reduce the additional reactions caused by long-term use of morphine and other opioids.

Opioids are known to activate cAMP production in cells, and long-term use of opioids leads to hypersensitization of adenylyl enzyme. Further the cAMP-dependent signaling pathway has a key influence on opioid-related long-term effects including tolerance, dependency, and other factors (see Li et al., 2006; Brust et al., 2017).

Technical Means to Problems

To complete the above invention, the present inventors have surprisingly discovered in research that three compounds NB001, NB010, and NB011 of the present disclosure can be used to reduce additional reactions caused by long-term use of opioids, thus completing the present invention.

NB001 of the present disclosure, i.e., 5-((2-(6-amino-9H-purin-9-yl)ethyl)amino)pentane-1-ol, has the following structure:

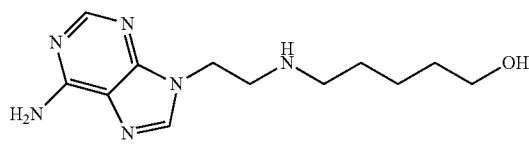

5-((2-(amino-9H-purin-9-yl)ethyl)amino)pentan-1-ol

NB010 of the present disclosure, i.e., 6-amino-9-(2-p-methoxy-ethyl)-9H-purine-8-thiol, has the following chemical structure:

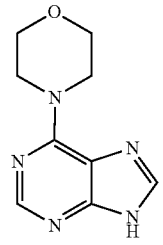

6-amino-9-(2-p-methoxy-ethyl)-9H-purine-8-thiol

NB011 of the present disclosure, i.e., 4-(9H-purin-6-yl) morpholine (also known as 6-morpholin-4-yl-7H-purine) has the following chemical structure:

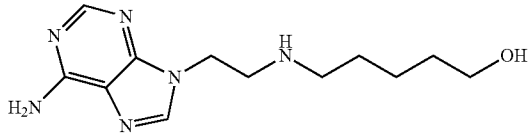

6-morpholin-4-yl-
7H-purine

According to the present invention, the following contents are provided:
(1) A pharmaceutical composition for treating pain, comprising:
opioids, and
at least one selected from the group consisting of NB001, NB010, or NB011,
the NB001, i.e., 5-((2-(6-amino-9H-purin-9-yl)ethyl)amino) pentane-1-ol, has the following structure:

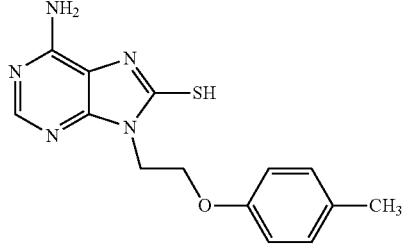

5-((2-(6-amino-9H-purin-9-yl)ethyl)amino)pentan-1-ol the NB010, i.e., 6-amino-9-(2-p-methoxy-ethyl)-9H-purine-8-thiol, has the following chemical structure:

6-amino-9-(2-p-methoxy-ethyl)-9H-purine-8-thiol the NB011, i.e., 4-(9H-purin-6-yl)morpholine (also known as 6-morpholin-4-yl-7H-purine) has the following chemical structure:

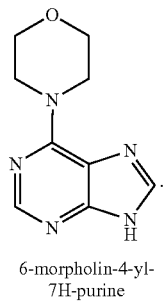
6-morpholin-4-yl-
7H-purine (2) The pharmaceutical composition according to (1), wherein the opioids is morphine.

(3) The pharmaceutical composition according to (1), wherein the three compounds of NB001, NB010, or NB011 further comprises a pharmaceutically acceptable salt or solvate thereof.

(4) Use of a pharmaceutical composition for preparing a medicament in the treatment of pain, the pharmaceutical composition comprising:

opioids, and at least one selected from the group consisting of NB001, NB010, or NB011, the NB001, i.e., 5-((2-(6-amino-9H-purin-9-yl)ethyl)amino)pentane-1-ol, has the following structure:

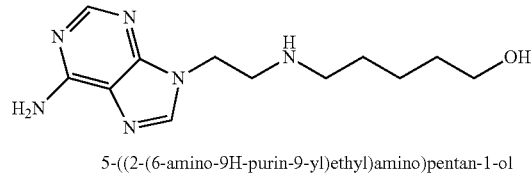 [SMILES: Nc1ncnc2c1ncn2CCNCCCCCO]
5-((2-(6-amino-9H-purin-9-yl)ethyl)amino)pentan-1-ol the NB010, i.e., 6-amino-9-(2-p-methoxy-ethyl)-9H-purine-8-thiol, has the following chemical structure:

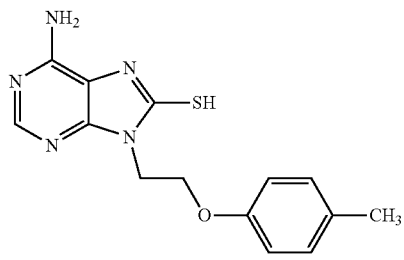
6-amino-9-(2-p-methoxy-ethyl)-9H-purine-8-thiol the NB011, i.e., 4-(9H-purin-6-yl)morpholine (also known as 6-morpholin-4-yl-7H-purine) has the following chemical structure:

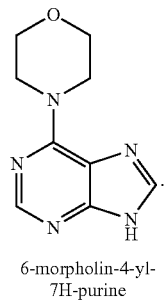 [SMILES: c1nc(N2CCOCC2)c2nc[nH]c2n1]
6-morpholin-4-yl-
7H-purine (5) The pharmaceutical composition according to (4), wherein the opioids is morphine.

(6) The pharmaceutical composition according to (4), wherein the three compounds of NB001, NB010, or NB011 further comprises a pharmaceutically acceptable salt or solvate thereof.

(7) A method for treating pain, wherein

Applying opioids, in combination with, at least one selected from the group consisting of NB001, NB010, or NB011, and a pharmaceutically acceptable salt or solvates thereof, the NB001, i.e., 5-((2-(6-amino-9H-purin-9-yl)ethyl)amino)pentane-1-ol, has the following structure:

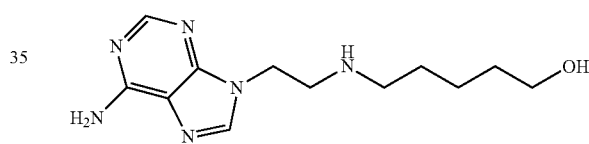
5-((2-(6-amino-9H-purin-9-yl)ethyl)amino)pentan-1-ol the NB010, i.e., 6-amino-9-(2-p-methoxy-ethyl)-9H-purine-8-thiol, has the following chemical structure:

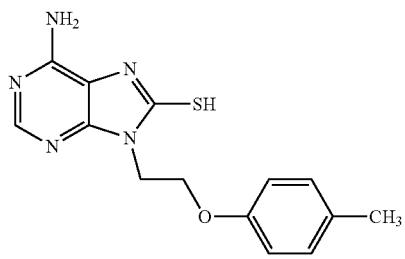
6-amino-9-(2-p-methoxy-ethyl)-9H-purine-8-thiol the NB011, i.e., 4-(9H-purin-6-yl)morpholine (also known as 6-morpholin-4-yl-7H-purine) has the following chemical structure.

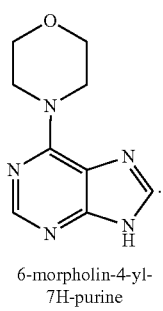

6-morpholin-4-yl-
7H-purine (8) The pharmaceutical composition according to (1), wherein the opioids is morphine.

The invention further provides (9) A pharmaceutical composition for treating anxiety caused by neuropathic pain and anxiety and depression associated with other diseases, the pharmaceutical composition containing at least one of three compounds of NB001, NB010, or NB011.

(10) The pharmaceutical composition according to (9), the three compounds of NB001, NB010, or NB011 further comprises a pharmaceutically acceptable salt or solvate thereof.

(11) A pharmaceutical composition for treating chronic visceral pain and related anxiety and depression, the pharmaceutical composition containing at least one of three compounds of NB001, NB010, or NB011.

(12) A pharmaceutical composition for treating an itching response caused by chronic use of morphine, the pharmaceutical composition containing at least one of three compounds of NB001, NB010, or NB011.

According to the present invention, NB001 has an enhanced effect on the analgesic effect of chronic use of morphine or other opiate compounds and can reduce tolerance. Combining morphine can reduce the dose of morphine required to produce similar levels of pain relief.

The treatment of the present invention can also be used to enhance morphine analgesic effect and/or reduce morphine tolerance in patients treated with morphine. Morphine tolerance (loss of morphine analgesia) may occur in patients with long-term use of morphine. Repetitive use of morphine over several days or weeks in humans and animals results in reduced analgesia.

Another aspect of the present invention relates to novel compounds NB010 and NB011 as AC1&8 inhibitors. This is particularly important because both AC1 and AC8 activity have been proposed as key to opioid-induced sensitization. Accordingly, inhibition of AC1 and AC8 activity may be an ideal choice for reducing opium-induced tolerance, addiction, and other effects. In the present invention, it is proposed to presume the principle of action of NB001, NB010, and NB011 because the AC1 and AC8 activities are effectively suppressed, while not all compounds that inhibit AC1 and AC8 have the effects of the present invention. NB010 and NB011 may be used to increase the analgesia of chronic use of morphine or other opiate compounds so as to reduce tolerance. Combining morphine can reduce the dose of morphine required to produce similar levels of pain relief.

The present invention further provides a human a treatment for morphine tolerance by administering an effective amount of a compound that inhibits AC1 or AC1&8 activity to the human in need thereof. Usually such a human has developed morphine tolerance during the treatment of chronic pain using morphine. NB010/NB011 may be used to reduce additive reactions caused by long-term use of morphine and other opiates.

In chronic pain such as neuropathic pain, cancer pain, patients may take pain medicaments for long time. In addition, the side effect of morphine treatment may be itching. NB010/NB011 may be used to reduce itching response caused by chronic use of morphine.

NB010/NB011 may be used to reduce emotional anxiety/depression caused by injury. NB010 and NB011 may be used to reduce itching that may be caused by chronic use of opiates (such as morphine) or damage. The present invention can encompass the use of NB010 and NB011 in general for anti-itching.

It is known that both AC1 and AC8 are involved in ethanol-induced sensitivity (Maas et al., 2005), and accordingly, NB010 and NB011 may be used to treat ethanol-related addiction, sensitivity and other symptoms.

It has been reported that AC1 and AC8 are involved in cocaine sensitization (DiRocco et al., 2009), and accordingly, the present inventors propose to use NB010 and NB011 to treat addiction behaviors related to the chronic use of cocaine and the like.

The compounds of the present invention may also be present in the form of pharmaceutically acceptable salts. For use in medicine, the salts of the compounds of this invention refer to non-toxic "pharmaceutically acceptable salts" (Ref International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient.

The pharmaceutical composition according to the present invention may be present in the form used for parenteral, oral, rectal, replacement or transdermal administration.

Thus, they will be presented in the form of injectable solutions or suspensions or multiple dose vials in the form of ordinary or coated tablets, dragees, wafer capsules, gel capsules, pills, cachets, powders, suppositories, or rectal capsules, for transdermal use in polar solvents, or for fixed use.

Suitable excipients for this application are cellulose or microcrystalline cellulose derivatives, alkaline earth metal carbonates, magnesium phosphates, starches, modified starches and lactose in solid form.

For rectal use, cocoa butter or polyethylene glycol stearate is a preferred excipient.

For parenteral use, water, aqueous solutions, physiological saline and isotonic solutions are the most suitable carriers for use. It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose. The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain as mentioned in the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression ana KarKinson s disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, *geniculate* neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

DETAILED DESCRIPTION OF THE PREFERRED EMBODIMENTS

NB001, 5-((2-(6-amino-9H-purin-9-yl)ethyl)amino)pentane-1-ol, has molecular formula C12H20N6O, and molecular weight 264.33. Available from Sigma 686301-48-4.

NB010, 6-amino-9-(2-p-methoxy-ethyl)-9H-purine-8-thiol has the following chemical structure:

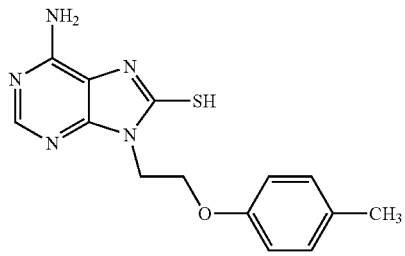 [SMILES: Cc1ccc(OCCn2c(S)nc3c(N)ncnc32)cc1]

A product available from Asinex LTD under BAS03384.

NB01 1,4-(9H-purin-6-yl)morpholine (also known as 6-morpholin-4-yl-7H-purine) has the following chemical structure:

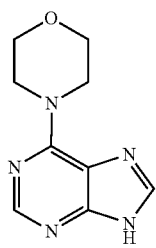

A product available from Maybridge company under JFD02793.

Pharmaceutically acceptable salts of the compounds having the indicated chemical formulae fall, within the scope of the present invention, into the definitions of Compound A and Compound B.

Example 1. Screening for AC1 & 8 Mixed Inhibitors

A set of biochemical screening tests were performed to search for potential AC1 and AC8 co-inhibitors (or referred to as AC1 & 8 inhibitors). AC1 or AC8 expressing cell lines were subject to cAMP assays, gene activation (pCREB) assays, and integrative physiological experiments to screen for potential compounds A and B acting on AC1 and AC8. It was found that both NB010 and NB011 produced significant inhibition of AC1 as well as AC8 activity at 100 μM (see Table 1). Regarding test methods, see Wang, H. S., et al., Identification of an Adenylyl Cyclase Inhibitor for Treating Neuropathic and Inflammatory Pain. Science Translational Medicine, 2011. 3(65).

TABLE 1

| Effects of NB010 and NB011 on the activity of adenylyl cyclase subtype 8 and 1 | | |
|---|---|---|
| | Percent Inhibition | |
| | AC8 | AC1 |
| NB010 (100 μM) | 88 ± 2% inhibition | 96 ± 4% |
| NB011 (100 μM) | 86 ± 2 | 91 ± 3% |

Example 2. Evaluation of NB010 and NB011 on Anxiety-Related Cortical LTP

Previous studies have indicated that AC1 and AC8 activity is required for synaptic LTP induced by repetitive stimulation (Zhuo, 2016). To evaluate the effects of NB010 and NB011 on AC1 and AC8 activity in neurons, two forms of LTP in ACC cortical slices of adult mice were recorded.

Figure 1:
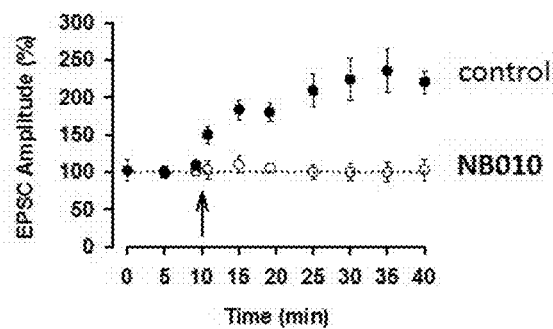
FIG. 1 Inhibition of pre-LTP and post-LTP in ACC using AC1 & 8 inhibitor NB010.
Figure 1:
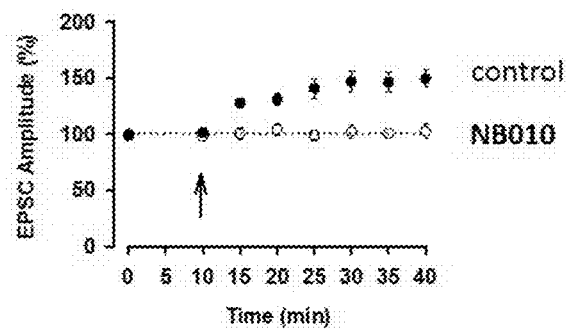
Figure 2:
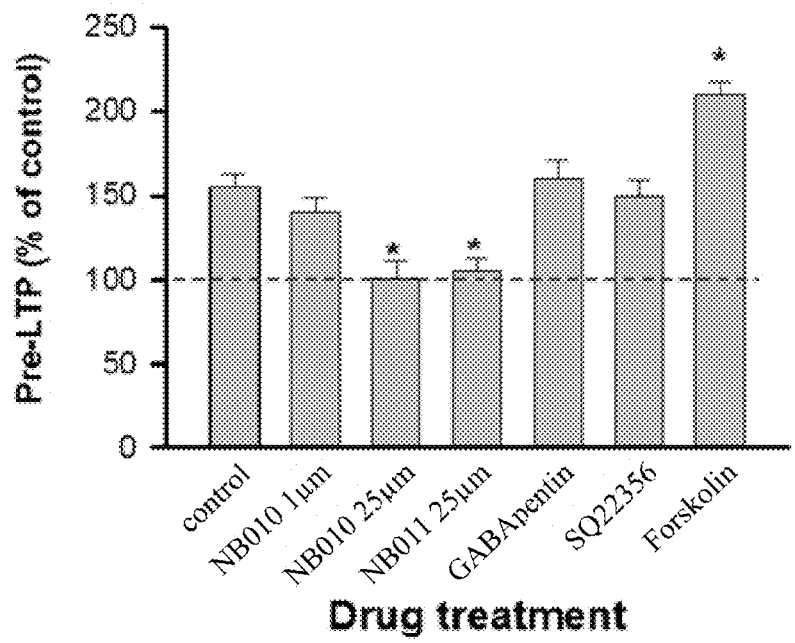
FIG. 2 The effect of inhibition of AC1/8 by different reagents on pre-LTP in ACC.

As above-mentioned, 6 burst stimulation induced potentiation of synaptic responses for at least 40 min (FIG. 1A, n=8 slices). Induction of ACC LTP can be blocked by pretreatment with NB010 (25 μM) (FIG. 1A, n=5 slices). Similar results were found with NB011 (FIG. 2, n=6 slices). In contrast, a non-selective AC inhibitor SQ22356 in the same dose did not cause a significant decrease in pre-LTP (FIG. 2, n=5). In contrast, pre-LTP was not blocked by using GABApention (25 μM) (n=5).

A recent report for ACC (Chen et al., 2014) also found that GABApention does not affect ACC LTP. Interestingly, forskolin (10 μM) resulted in a slight increase in pre-LTP (FIG. 2), indicating that AC activation is critical for pre-LTP. These findings indicate that both NB010 and NB011 can inhibit AC1 and AC8 activity in adult mouse neurons. This proves that NB010 and NB011 may be used to treat anxiety caused by injury.

Recent studies have indicated that anxiety caused by injury may be related to pre-LTP (Koga et al., 2015; Zhuo, 2016), therefore the present inventors decided to test the effect of NB010 and NB011 on pre-LTP. And both compounds were found to inhibit pre-LTP (FIG. 1). For detailed test process, see Koga, K., et al., Coexistence of Two Forms of LTP in ACC Provides a Synaptic Mechanism for the Interactions between Anxiety and Chronic Pain. Neuron, 2015. 85(2): p. 377-389.

FIG. 1 Inhibition of pre-LTP and post-LTP in ACC using AC1 & 8 inhibitor NB010, where (A) Post-LTP was induced in the control slices (filled circles; n=8), whereas post-LTP was blocked by the application of NB010 (25 μM) solution (n=5); (B) Pre-LTP was induced in the control slices (filled circles; n=8); whereas pre-LTP was blocked by the application of NB010 (25 μM) solution (n=5). FIG. 2 showed the effect of inhibition of AC1/8 by different reagents on pre-LTP in ACC. where, the data showed that the induction of pre-LTP was enhanced in the last 5 minutes during 45 minutes. * indicates a significant difference compared to the control group (where NB010 and NB011 resulted in a decrease while forskolin resulted in an increase).

Example 3. Behavioral Effects of AC1 and AC1&8 Inhibitors on Morphine Tolerance First, the present inventors intended to examine whether AC1 knockout mice will affect the morphine tolerance caused by repetitive injections of morphine. According to previous reports by the inventors, morphine was injected (10 mg/kg, s.c.) daily for 7 days to measure morphine-induced tolerance. It was found that in AC1 knockout mice, morphine produced significant great analgesic effects as compared with saline-treated wild-type mice (n=5-8 mice: day 7: control mice, MPE 18±6%, AC1 KO, 40±8%; P<0.05). These results indicate that inhibiting AC1 activity may be beneficial for reducing morphine tolerance. Next a selective AC1 inhibitor NB001 (5 mg/kg, i.p.) was used to treat wild-type mice with morphine. Both nociceptive hotplate and tail-flick response latencies were recorded. It was found that NB001 co-application produced a significant effect on response latencies after chronic morphine treatment (p<0.005) (FIG. 3).

Previous studies from AC1 and AC8 double knockout mice found that morphine tolerance was significantly reduced (Li et al., 2006). The inventors expected that AC1 &8 inhibitors may also produce beneficial effects in reducing morphine tolerance. Similarly, pretreatment with NB010 or NB011 (5 mg/kg, i.p.) both produced significant greater analgesic effects at 7 days after morphine injections (n=5-8 mice, p<0.05 as compared with control treatment in each case). For detailed test methods, see Li, S., Lee, M L, Bruchas, M R, Chan, G C, Storm, D R, and Chavkin, C. (2006). Calmodulin-stimulated adenylyl cyclase gene deletion effects morphine responses. Mol Pharmacol 70, 1742-1749.

Figure 3:
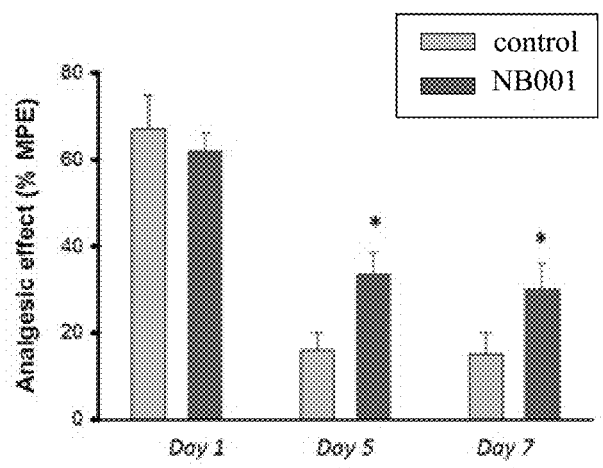
FIG. 3 Morphine tolerance induced by repeated injections of morphine (10 mg/kg) was reduced by using the AC1 inhibitor NB001 (5 mg/kg).

FIG. 3 showed that morphine tolerance induced by repeated injections of morphine (10 mg/kg) was reduced by using the AC1 inhibitor NB001 (5 mg/kg).

Accordingly, the inventors expected that both the AC1 inhibitor NB001 and the AC1&8 inhibitors NB010 and NB011 may be useful for enhancing morphine analgesic effect, thereby enable the repetitive use of morphine.

Figure 4:
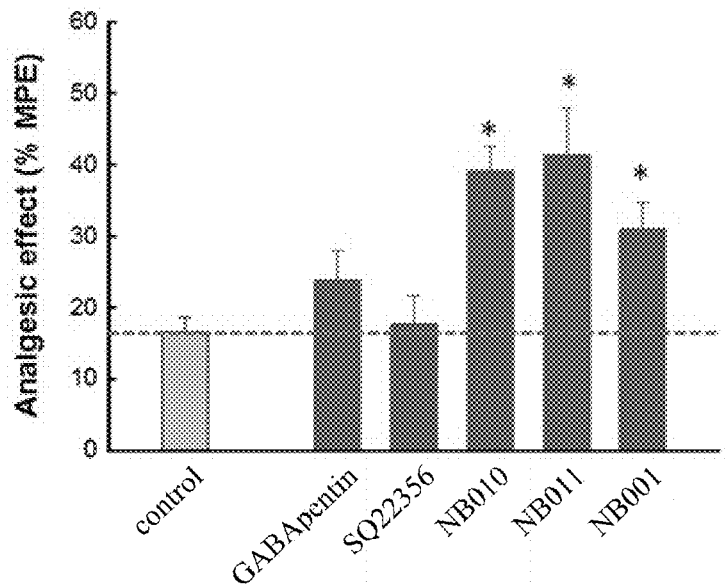
FIG. 4 NB010 and NB011 produced significant effects in reversing morphine tolerance.

As shown in FIG. 4, NB010 and NB011 produced significant effects in reversing morphine tolerance at 7 days after morphine injection (10 mg/kg) (n=5-7 mice). In contrast, 100 mg/kg of GABApentin did not produce a significant effect (n=6 mice). In addition, the effect of the non-selective AC inhibitor SQ22356 was also tested and no significant effect was found at the same dose, indicating that selective inhibition of AC1/AC8 is critical.

To further test the role of AC1/AC8 in morphine tolerance, AC activator forskolin was applied and it was found that morphine produced tolerance faster in mice (n=3 mice) 3 days after repetitive administration of morphine.

For the AC1 inhibitor NB001 (5 mg/kg) and the AC1/AC8 inhibitor NB010 or NB011 (5 mg/kg), morphine tolerance induced by repetitive injections of morphine (10 mg/kg) 7 days after repetitive morphine injections reduced. GABApentin (100 mg/kg) or SQ22356 (5 mg/kg) did not produce any significant effect.

To test possible dose-related effects, the NB compound were applied at a lower dose of 1 mg/kg; no significant effect was found with NB001/NB010/NB011, indicating that the effect produced was dose-related.

Example 4. Conditioned Place Preference (CPP) to Morphine

Conditioned Place Preference (CPP) was used to verify the reduced response of CREB mutant mice to the beneficial effects of morphine (Walters and Blendy, 2001). Morphine CPP was subsequently induced in saline-treated and inhibitor treated mice. It was found that mice treated with NB001 (5 mg/kg, ip) spent significantly less time exploring the morphine-paired side of the chamber than saline-treated mice, indicating that AC1 played a role in the enhanced properties of morphine (p<0.05). There is no significant difference in their initial preference for either side of the chamber. For the detailed test methods, see Walters C L, Blendy J A (2001) Different requirements for cAMP response element binding protein in positive and negative reinforcing properties of drugs of abuse. J Neurosci 21:9438-9444.

Figure 5:
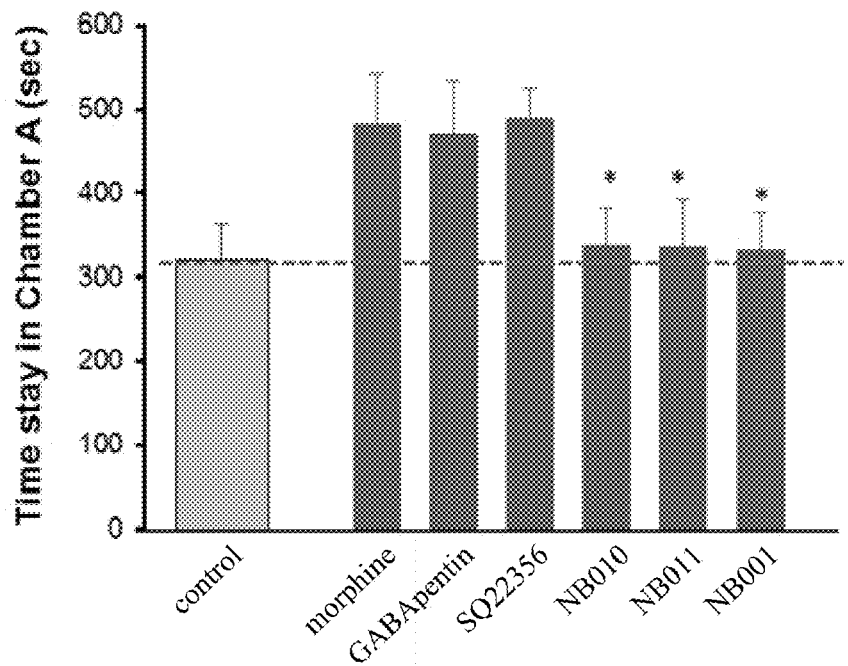
FIG. 5 The result of the conditioned place preference experiment.

For the conditioned place preference experiment of morphine, the inventors found that NB00I caused a significant reduce in morphine-induced preference. Both NB010 and NB011 (5 mg/kg) are similar to NB001 (FIG. 5). In contrast, a non-selective AC inhibitor SQ22356 in the same dose did not produce any inhibition (FIG. 5). It indicated that AC1/AC8 inhibition is selective. The effect of GABApention at 100 mg/kg was also tested. As a result shown in FIG. 5, morphine (10 mg/kg) was repeatedly used to induce place preference behavior after 9 days, and the effects of applying the AC1 inhibitor NB001, AC1/8 inhibitor NB010 or NB011 (5 mg/kg) were significant. GABApentin (100 mg/kg) or SQ22356 (5 mg/kg) did not produce any significant effect.

In addition, the test results also showed (not shown in the figure) that when the dose of NB001/NB010/NB011 was reduced to 1 mg/kg, the expected effect was not produced, so the effect of NB001/NB010/NB011 was dose-dependent (n=3-5 mice). Forskolin (5 mg/kg) did not produce any inhibitory effect, and the results also showed a slight increase in selection time (n=3 mice).

Example 5. Anxiety Behavior Test

Figure 6:
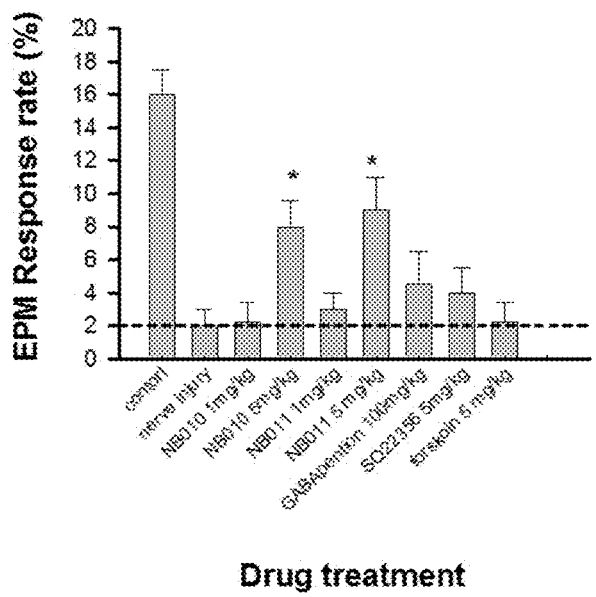
FIG. 6 The effect of different agents on anxiety caused by nerve injury.

As previously mentioned, the inventors found that nerve injury caused anxiety behavior in the EPM test (Koga et al., 2015; see FIG. 6). The inventors therefore examined whether NB010 or NB011 can reduce anxiety and other behaviors since both inhibitors prevent anxiety-related pre-LTP. As expected, NB010 or NB011 (5 mg/kg) produced significant reduction in anxiety responses caused by nerve injury (P<0.05 in each case, n=6 mice for each agent) (see FIG. 6).

At lower doses (1 mg/kg), NB010 (see FIG. 6) did not significantly decrease. Similar result was obtained with NB011 of 1 mg/kg. Neither GABApentin (100 mg/kg, i.p.) nor SQ22356 (5 mg/kg) significantly reduced behavioral anxiety (FIG. 3). The use of forskolin (5 mg/kg) did not further increase anxiety, which may be due to the production of saturation effect (FIG. 6).

For detailed experimental methods, see Koga, K., et al., Coexistence of Two Forms of LTP in ACC Provides a Synaptic Mechanism for the Interactions between Anxiety and Chronic Pain. Neuron, 2015. 85(2): p. 377-389.

FIG. 6 shows the effect of different agents on anxiety caused by nerve injury. The use of AC1 & 8 inhibitor NB010/NB011 (5 mg/kg, i.p.) reduced anxiety caused by nerve injury (7 days after injury). At low doses of 1 mg/kg, neither NB010 nor NB011 affected anxiety. The use of GABApentin (100 mg/kg) or SQ22356 (5 mg/kg) had no significant effect. EPM test was used in this example to assess the anxiety state.

Itching Response

Figure 7:
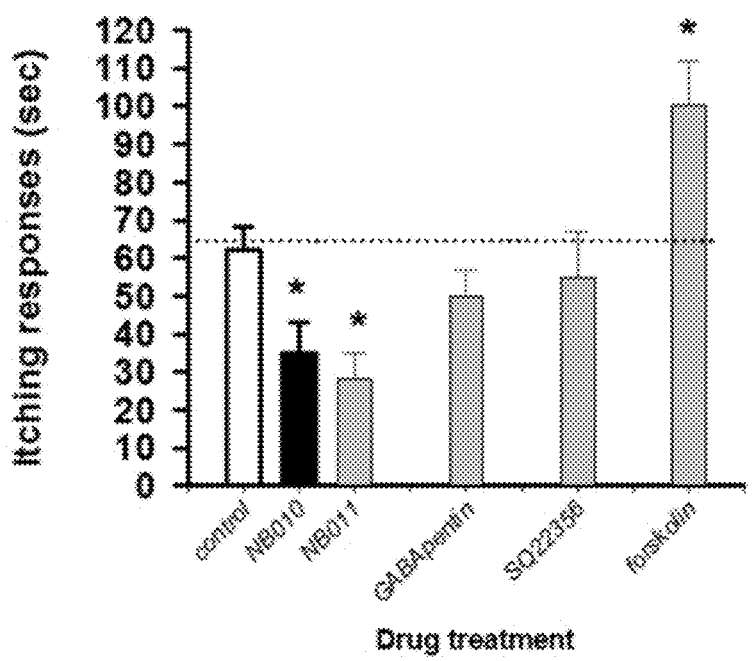
FIG. 7 The result of Itching response test.

It is well known that itching is often caused by a variety of diseases, including the chronic use of opioids. To evaluate if the inhibition of AC1 and AC8 may reduce itching response, the inventors evaluated the effect of NB010 and NB011 on behavioral itching response to injection of Compound A. A specific test method refers to U.S. Patent Publication No. US20110098295 A1, and as a result, it was found that the total scratching responses induced by intradermal injection of compound 48/80 (100 µg/50 µl) was found to be significantly reduced in mice receiving the injection of NB010 or NB011 pretreatment (n=6 mice) as compared with wild-type mice (n=7) (FIG. 7). The application of GABApention (100 mg/kg) did not cause a significant reduction in the itching response (FIG. 7). SQ22356 also did not show significantly reduction at the dose tested (5 mg/kg, ip). In contrast, the application of forskolin (5 mg/kg) significantly enhanced the behavioral itching response (FIG. 7). FIG. 7 shows the effect of different agents that affect the cAMP pathway on behavioral itching responses in mice. The application of NB010 or NB011 significantly reduced the itching response induced by histamine releasing compound 40/80 in adult mice. In contrast, neither GABApentin nor SQ22356 produce any significant effect. Forskolin is an AC activator that significantly enhances the itching response. *P<0.05 compared to control.

Experimental Animals

AC1 and AC8 KO mice, see Wei F, Qui C S, Kim S J, et al. Genetic elimination of behavioral sensitization in mice lacking calmodulin-stimulated adenylyl cyclase. Neuron. 2002; 36(4): 713-726, were bred for several generations (F8-F12) on C57B1/6 background. Control wild-type (WT) mice were adult male (8-12 weeks old) C57B11/6 mice from Charles River. At the end of the experiment, animals were treated with excess inhalation of anesthetic (halothane). Animals were housed on a 12 h: 12 h light: dark cycle with food and water available ad libitum.

Biochemical Screening Tests for Novel Inhibitors for AC8 and AC1

For the AC8 expression vector pcDNA3-AC1 transfection, HEK293 cells were plated onto a 60 mm diameter petri dish at a density of $1\times10^6$ per plate, grown overnight, and transfected with pcDNA3-AC1 (0.8 µg DNA per plate) by Lipofectamine 2000 (Invitrogen). Stable transfected clones were selected and maintained in media containing 0.8 mg/ml G418 (Invitrogen, CA). For transient expression of other AC isoforms in HEK293 cells, HEK293 cells were seeded in 96-well tissue culture dishes and transfected with AC5 plasmid respectively, and subject to experiment 48 hours after transfection.

HEK293 cells expressing ACs were harvested and lysed in 0.1 M HCl after different treatments. Direct cAMP measurements were performed using a direct cAMP enzyme immunoassay kit (Assay Designs, MI) and optical density values were measured at 405 nm by a microplate reader. Phosphodiesterase was inhibited by the addition of 1 mM 3-isobutyl-1-methylxanthine (Sigma, MO) to cultures.

CRE Luciferase Reporter Gene Assay

HEK293 cells were subcultured into 96-well plates in the absence of antibiotics and grown overnight, and transfected with pGL3-CRE firefly luciferase and pGL3-CMV-adrenergic luciferase constructs (0.25 µg DNA per well) by Lipofectamine 2000 reagent. The transfected cells were incubated overnight and the medium was changed to DMEM containing 10% fetal calf serum. After 48 hours, cells were treated with 10 µM forskolin, 10 µM A23187 and 2 mM CaCl2), or a combination of 10 µM forskolin, 10 µM A23187 and 2 mM CaCl2, in the absence or presence of each chemical tested at the concentration of 100 µM. At the end of 6 hours, the cultured cells were harvested and assayed for luciferase activity by Dual Luciferase Reporter Assay System (Promega). Relative light units were measured using a SIRIUS luminometer.

Whole Cell Patch Clamp Recording

Coronal brain sections (300 µm) at ACC level were prepared using standard methods (Wu et al., 2005). The sections were transferred to an immersion recovery chamber containing oxygen (95% 02 and 5% CO2) artificial cerebrospinal fluid (ACSF) (containing mM: 124 NaCl, 2.5 KCl, 2 CaCl2, 1 MgSO4, 25 NaHCO3, 1 NaH2PO4, 10 glucose) at room temperature for at least 1 hour. Experiments were performed in a recording chamber on a stage of a BX51W1 microscope equipped with infrared DIC optics for visualization. Excitatory postsynaptic currents (EPSCs) were recorded from layer II/III neurons with an Axon 200B amplifier (Axon Instruments, CA), and the stimulations were delivered by a bipolar tungsten stimulating electrode placed in layer V of the ACC. Alpha-amino-3-hydroxy-5-methylisoxazole-4-propionic acid (AMPA) receptor-mediated EPSCs were induced by repetitive stimulations at 0.05 Hz and neurons were voltage clamped at −70 mV in the presence of AP5 (50 µM). The recording pipettes (3-5 MΩ) were filled with a solution containing (in mM): 145 K-gluconate, 5 NaCl, 1 MgCl2, 0.2 EGTA, 10 HEPES, 2 Mg-ATP, 0.1 Na3-GTP and 10 phosphocreatine disodium and was adjusted to pH 7.2 with KOH. The internal solution (in mM: 140 cesium methanesulfonate, 5 NaCl, 0.5 EGTA, 10 HEPES, 2 MgATP, 0.1 Na3GTP, 0.1 spermine, 2 QX-314 bromide and 10 phosphocreatine disodium (adjusted to pH 7.2 with CsOH) was used in the rectification of AMPA receptor-mediated transmission experiment. For miniature EPSC (mEPSC) recordings, 0.5 µM TTX was added in the perfusion solution. Picrotoxin (100 µM) was always present to block GABAA receptor-mediated inhibitory synaptic currents in all experiments. Access resistance was 15-30 MΩ and monitored throughout the experiment. Data were discarded if access resistance changed by more than 15% during the experiment. Data were filtered at 1 kHz, and digitized at 10 kHz.

Conditioned Place Preference Experiment

A chamber with two distinct contextual environments (different walls, floor and smell) was used (MED-associates, St. Albans, Vt.). On the first day of test, animals were allowed to freely explore both sides of the chamber for 30 min and data were used to divide animals into groups of approximately equal bias. Over the next eight days, each animal was given either 10 mg/kg morphine or an equivalent volume of saline on alternate days at different sides of the chamber. Animals were confined to a specific side of the chamber for 30 minutes. After conditioning, all animals were injected with saline and allowed to freely explore both sides of the chamber for 30 minutes. Place preference was defined as an increase in the time spent in the morphine-paired side after conditioning as compared to before.

Neuropathic Pain Model

A model of neuropathic pain was induced by connecting a common peroneal nerve (CPN) as previously described (Li et al., 2010). Briefly, mice were anesthetized by intraperitoneal injection of a mixture saline of ketamine (0.16 mg/kg; Bimeda-MTC) and xylazine (0.01 mg/kg; Bayer). CPN was visible between the anterior and posterior groups of muscles running almost transversely. The chronic CPN was slowly connected to the chromic gut suture 5-0 (Ethicon) until the contraction of the dorsiflexors of the foot was visible as twitching of digits. Mechanical allodynia test was performed on 3rd, 7th and 14th postoperative day. The experiment was blinded and different individuals were responsible for the surgery and the measurements of the mechanical sensitivity of mice.

Mechanical Allodynia Test

Mice were placed in a circular container and adapted for 30 minutes before test. Mechanical allodynia was evaluated based on the responsiveness of hind paws to the application of von Frey filaments (Stoelting) to the bending point. Positive responses included licking, biting, and sudden withdrawal of the hind paws. Experiments were conducted to characterize the threshold stimulus. Mechanical pressure (force, 0.008 g) from 1.65 filaments was found to be harmless in naïve mice. This filament was then used to test mechanical allodynia.

What is claimed is:

1. A method of reducing morphine tolerance in a human patient, comprising the steps of:
    i) repetitively administering morphine to the human patient; and
    ii) administering to the human patient an analgesically effective dose of 5-((2-(6-amino-9H-purin-9-yl)ethyl)amino)pentane-1-ol (NB001) or a pharmaceutically acceptable salt or solvate thereof,
    wherein the NB001 or pharmaceutically acceptable salt or solvate thereof suppresses AC1 activity and increases analgesia of the morphine, and
    wherein the human patient has osteoarthritis, rheumatoid arthritis, or a toothache.

2. The method of claim 1, wherein the NB001 or the pharmaceutically acceptable salt or solvate thereof is administered in combination with 6-amino-9-(2-p-methoxyethyl)-9H-purine-8-thiol (NB010).

3. The method of claim 2, wherein the NB001 or the pharmaceutically acceptable salt or solvate thereof administered in combination with NB010 is further administered in combination with 6-morpholin-4-yl-7H-purine (NB011).

4. The method of claim 1, wherein the NB001 or pharmaceutically acceptable salt or solvate thereof is administered orally as tablets containing 0.01, 10.0, 50.0, 100, 150, 200, 250, or 500 milligrams of NB001 or a pharmaceutically acceptable salt or solvate thereof.

5. A method of reducing morphine tolerance in a human patient, comprising the steps of:
   i) repetitively administering morphine to the human patient; and
   ii) administering to the human patient a pharmaceutical composition comprising an analgesically effective dose of 5-((2-(6-amino-9H-purin-9-yl)ethyl)amino)pentane-1-ol (NB001) or a pharmaceutically acceptable salt or solvate thereof,
   wherein the NB001 or pharmaceutically acceptable salt or solvate thereof suppresses AC1 activity and increases analgesia of the morphine, and
   wherein the human patient has osteoarthritis, rheumatoid arthritis, a migraine, a headache, a toothache, or a burn.

6. The method of claim 5, wherein the NB001 or pharmaceutically acceptable salt or solvate thereof is administered in combination with 6-amino-9-(2-p-methoxy-ethyl)-9H-purine-8-thiol (NB010).

7. The method of claim 6, wherein the NB001 or pharmaceutically acceptable salt or solvate thereof administered in combination with NB010 is further administered in combination with 6-morpholin-4-yl-7H-purine (NB011).

8. The method of claim 5, wherein the NB001 or pharmaceutically acceptable salt or solvate thereof is administered orally as tablets containing 0.01, 10.0, 50.0, 100, 150, 200, 250, or 500 milligrams of NB001 or a pharmaceutically acceptable salt or solvate thereof.

* * * * *